United States Patent [19]

Lin

[11] Patent Number: 4,866,177

[45] Date of Patent: Sep. 12, 1989

[54] PROCESS FOR ONE-STEP SYNTHESIS OF AMIDES

[75] Inventor: Jiang-Jen Lin, Round Rock, Tex.

[73] Assignee: Texaco Inc., White Plains, N.Y.

[21] Appl. No.: 934,380

[22] Filed: Nov. 24, 1986

[51] Int. Cl.$^4$ .............................................. C07B 43/06
[52] U.S. Cl. ..................................... 544/387; 564/132; 544/386
[58] Field of Search .................. 564/132; 544/386, 387

[56] References Cited

U.S. PATENT DOCUMENTS

| | | | |
|---|---|---|---|
| 2,422,631 | 6/1947 | Olin et al. | 564/132 X |
| 2,422,632 | 6/1947 | Olin et al. | 564/132 |
| 2,542,766 | 2/1951 | Gresham | 564/132 |
| 2,648,685 | 8/1953 | Reppe | 564/132 X |
| 3,168,553 | 2/1965 | Slaugh | 564/132 X |
| 3,679,689 | 7/1972 | Fenton | 564/249 |
| 3,947,458 | 3/1976 | Iqbal | 564/132 X |
| 4,297,481 | 10/1981 | Jachimowicz | 528/396 X |
| 4,312,965 | 1/1982 | Jachimowicz et al. | 528/396 X |
| 4,313,893 | 2/1982 | Pesa et al. | 564/132 X |
| 4,525,288 | 6/1985 | Schlicht | 252/32.7 E |
| 4,551,257 | 11/1985 | Horodysky | 252/32.7 E |
| 4,657,984 | 4/1987 | McEntire et al. | 525/333.1 X |

FOREIGN PATENT DOCUMENTS 60-96696 5/1985 Japan.
60-99074 6/1985 Japan.

OTHER PUBLICATIONS

Iwashita et al., *J. Org. Chem.*, vol. 36, No. 25 (1971), pp. 3937-3938.

Primary Examiner—Charles F. Warren
Assistant Examiner—Carolyn S. Greason
Attorney, Agent, or Firm—Jack H. Park; Kenneth R. Priem; Cynthia L. Kendrick

[57] ABSTRACT

A N-alkyl amide derivative is synthesized in one-step by reacting an olefin, nitrogen-containing compound and carbon monoxide with a catalyst comprising a rhodium-containing compound in the presence of water at a pressure of at least 500 psi and a temperature of at least 50° C.

4 Claims, No Drawings

PROCESS FOR ONE-STEP SYNTHESIS OF AMIDES

FIELD OF THE INVENTION

This invention relates to the one-step synthesis of various amides.

More particularly this invention uses a rhodium-containing catalyst for one-step direct synthesis of N-alkyl amides in high yield from olefins, primary or secondary amines or ammonia and carbon monoxide in the presence of water.

BACKGROUND OF THE INVENTION

The application of rhodium catalysts for synthesis of linear amides in high productivity appears to be a concept not previously researched in the art.

In *Journal of Organic Chemistry* 36, No. 25 (1971) 3927 Iwashita and Sakuraba describe a one-step synthesis of imidazoles using a rhodium catalyst, an olefin and ammonia by the route of olefin carbonylation in the presence of ammonia.

It is taught in the art that a cobalt catalyst can be used for the conversion of an unsaturated amide into a succinimide. A cobalt catalyst can also be used for imide and cyclic amide (lactam) synthesis. See J. Falbe New Synthesis With Carbon Monoxide, 1980, p. 285 and 415-419. In the same reference at page 420 there is a discussion of the use of rhodium catalyst for cyclic amide synthesis.

These references indicated that the carbonylation of a simple olefin in the presence of a primary amine to form a amide is generally affected by cobalt catalysts. Related reactions can be achieved by nickel or palladium catalysts. In the presence of hydrogen and a modified Rh catalyst, amines were produced from olefin and ammonia.

It was reported that, in the presence of $NH_3$ and a modified Rh catalyst, the carbonylation of alkenes produced substituted dihydropyridines under the described reaction conditions. (U.S. Pat. No. 3,679,689, June 7, 1970) The reaction can be represented by:

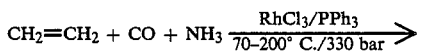

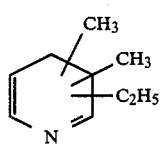

These references do not appear to address the one-step, direct synthesis of various substituted and non-substituted amides such as N,N-diethylpropionamide and propionamide by the reaction of the instant invention.

It is known that N-alkyl amides are potentially useful as lubricants (See U.S. Pat. Nos. 4,551,257 to Mobil and 4,525,288 to Texaco), cosurfactants (See U.S. Pat. No. 4,490,263 to Phillips Petroleum) and nonionic surfactants (Japan No. 60099-074 and Japan No. 60096-696). Also the non- or mono-substituted amides are useful as starting materials for the synthesis of amidoacids.

SUMMARY OF THE INVENTION

This invention concerns a method for synthesizing N-alkyl amides which comprises contacting a mixture of olefins, amines and carbon monoxide with a catalyst comprising a rhodium-containing compound, in the presence of water at a pressure of at least 500 psi and a temperature of at least 50° C. The reaction is exemplified by the reaction of an olefin such as ethylene, carbon monoxide, an amine such as diethylamine, piperazine, or ammonia and a rhodium-containing catalyst such as $Rh_2O_3$ or $HRh(CO)(PPh_3)_3$. The yield of alkyl amide products reaches as high as 95%.

DETAILED DESCRIPTION OF THE INVENTION

In the narrower and more preferred practice of this invention linear N-alkyl amides are prepared from a mixture of olefins, nitrogen-containing compounds and carbon monoxide by a process which comprises contacting said mixture with a catalyst system comprising a rhodium-containing compound in water at a temperature of at least 50° C. and a pressure of at least 500 psi until substantial formation of the desired amide has been achieved.

The reaction for producing an N-alkyl amide such as N,N-diethylpropionamide from ethylene and diethylamine can be represented by the following equation:

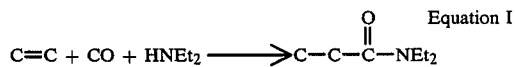

Where the nitrogen-containing compound used is ammonia the reaction can be represent by the following equation

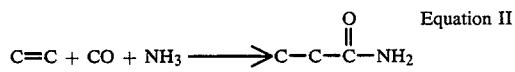

Where the nitrogen-containing compound used is piperazine as another example, the reaction can be represented by the following equation:

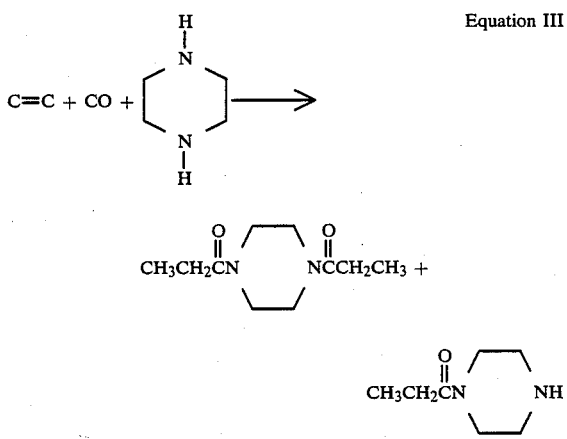

Recovery of the N-alkyl amides from the reaction product can be carried out in any convenient or conventional manner such as by distillation, extraction, filtration, crystallization, etc. In the embodiment of this invention the product was recovered by a simple distillation procedure. The product was identified by HMR and glc.

The catalyst system suitable for the practice of this invention comprises a rhodium-containing compound in water.

The rhodium-containing compound may take many different forms. For instance the rhodium could be added in the form of an oxide, a salt of a mineral acid, the salt of a suitable organic carboxylic acid or a carbonyl, hydrocarbonyl or derivative thereof.

Compounds which work well in the process of this invention include those where the rhodium is added to the reaction zone as a carbonyl, hydrocarbonyl or substituted carbonyl species. The preferred compound is hydrated rhodium oxide ($Rh_2O_3 5H_2O$).

As mentioned above the rhodium-containing catalyst is used in the presence of water. The amount of water used is 5~50 wt % in the reaction mixture. The presence of the water has the effect of activating the Rh catalyst.

The physical parameters which are desirable for the feedstock of this invention for producing N-alkyl amides can be described as follows:

The starting olefin substrates can be represented by the following structure

$R-CH=CH_2$

The R-group can be hydrogen or any alkyl, such as methyl, ethyl, hexyl or octyl, including branched alkyl, such as 2-ethyl-hexyl and cyclic alkyl. The preferred alpha olefins include ethylene, propylene, 1-butene, 1-hexene and 1-dodecene. Particularly good results are obtained using ethylene.

Suitable nitrogen-containing coreactants that are useful in the amidocarbonylation reaction can be any primary or secondary amines having the general structure:

$R_1R_2NH$ where the $R_1$ and $R_2$ groups may be a combination of aryl, alkyl, cyclic alkyl arylalkyl and alkylaryl hydrocarbonyl radicals, or hydrogen, including the methyl, ethyl, butyl, n-octyl, phenyl, benzyl and chlorophenyl groupings. Examples of suitable amine coreactants include dimethylamine, ethylamine, diethylamine, ammonia and piperazine. Good results were obtained using diethylamine and piperazine as the coreactant.

The carbon monoxide employed need not satisfy particular purity requirements although catalyst contaminants should be avoided if the reaction is intended to continue over an extended period. Particularly in continuous operations, but also in batch experiments, the carbon monoxide and hydrogen gas may also be used in conjunction with up to 10% by volume of one or more other gases. These other gases may include one or more inert gases such as argon, nitrogen and the like or they may include gases that may, or may not, undergo reaction under carbon monoxide hydrogenation conditions, such as carbon dioxide, hydrocarbons, such as methane, ethane, propane and the like, ethers, such as dimethyl ether, methyl ethyl ether and diethyl ether, alkanols, such as methanol, and the like.

As characterized above, this process is operated as a homogeneous liquid phase mixture. The reaction can be operated in water or water and a solvent. Preferred inert solvents are those which permit at least partial dissolution of the rhodium catalyst precursors, the nitrogen-containing compound and the olefin. These are generally polar solvents, of the ester, ether, ketone, amide, sulfoxide or aromatic hydrocarbon type, for example.

Methyl and ethyl acetate are examples of suitable solvents. Other polar solvents are ethers, such as p-dioxane, methyl tertiary butyl ether, methyl tertiary amyl ether or tetrahydrofuran, tertiary amides, such as dimethyl formamide, and dimethyl sulfoxide.

The preferred solvent is p-dioxane.

In all these synthesis in order to achieve a high degree of selectivity the amount of carbon monoxide, olefin and nitrogen-containing compound present in the reaction mixture should be sufficient to at least satisfy the stoichiometry of the desired formation of N-alkyl amide acid as shown in Equations I-III above. Excess carbon monoxide over the stoichiometric amount may be present and is desirable.

The quantity of rhodium-containing compound to be used in the catalyst of the invention may vary. The process is conducted in the presence of a catalytically effective quantity of the active rhodium-containing compound which gives the desired product in reasonable yield. The reaction proceeds when employing as little as about 0.01 weight percent, and even lesser amounts of the rhodium-containing compound, based on the total weight of the reaction mixture. The upper concentration is dictated by a variety of factors including catalyst cost, partial pressures of carbon monoxide and hydrogen, operating temperature, etc. A rhodium-containing compound concentration of from about 0.01 to about 1.0 weight percent based on the total weight of the reaction mixture is generally desirable in the practice of this invention. The amount of water which contributes toward obtaining the desired product in reasonable yield can vary. The reaction proceeds when employing as little as about 1 weight percent and even lesser amounts, based on the total weight of the reaction mixture. A concentration of water of from about 1 to about 50 percent based on the total weight of the reaction mixture is desirable.

The operating conditions may vary over a wide range. The reaction temperature may vary from 25° C. to 300° C. The preferred temperature is from 80° C. to 200° C. The pressure may range from 1000 psi to 4000 psi or more.

In general good results are obtained using about 3000 psi, 150° C. and 4 hours.

The carbonylation reaction of this invention is best conducted in a carbon monoxide-rich atmosphere. The presence of hydrogen is not required. Small amounts of hydrogen in the system might actually increase the Rh catalyst activity. However, in some cases, it is believed that the presence of hydrogen can be detrimental to the desired reaction and causes side reactions. Therefore, pure carbon monoxide is preferred.

The desired products are alkyl amides, such as, for example propioamide, butanoamide, N,N-diethylpropionamide, N,N'-dipropionyl piperazine. Also formed are significant amounts of ester by-products. Each of these products, including by-products can be recovered from the reaction mixture by conventional means, e.g. crystallization or distillation.

The desired products of the synthesis using olefins and amines are, for example, N,N-diethylpropionamide, N,N'-dipropionyl piperazine and propionamide.

The novel process of the invention can be conducted in a batch, semi-continuous or continuous manner. The catalyst can be initially introduced into the reaction zone batchwise, or it may be continuously or intermittently introduced into such a zone during the course of the synthesis reaction. Operating conditions can be adjusted to optimize the formation of the desired N- alkyl amide product, and said material may be recovered by methods known to the art, such as filtration, recrystallization distillation, extraction and the like. A fraction rich in the catalyst components may then be recycled to the reaction zone, if desired, and additional products generated.

The products have been identified in this work by one or more of the following analytical procedures: viz, gas-liquid phase chromatography (glc), gas chromatography/infrared spectroscopy (GC/IR), nuclear magnetic resonance (nmr) and elemental analysis, or a combination of these techniques. Analysis have for the most part, been by molar weight; all temperatures are in degrees centigrade and all pressures in pounds per square inch (psi).

The yield (mole %) of N-alkyl amide product in this synthesis using an olefin and nitrogen-containing compound is estimated basis equation I using the formula:

$$\frac{\text{Moles of N-alkyl amides obtained}}{\text{Moles of amine charged}} \times 100\%$$

To illustrate the process of the invention, the following examples are given. Examples 1–8 demonstrate the method of using alpha olefins in the process of this invention. Examples demonstrate the embodiment using olefins and amines to produce liquid or solid derivatives. It is to be understood, however, that the examples are given in the way of illustration and are not to be regarded as limiting the invention in any way.

EXAMPLE 1

A glass-lined autoclave was charged with $Rh_2O_3 \cdot 5H_2O$ (0.025 g, 0.073 mmole), diethylamine (15 g, 205 mmoles), water (5.0 g) and p-dioxane (10.0 g). The reactor was assembled and then ethylene (10 g) charged through a pressure sample bomb. The system was pressured with carbon monoxide to 2000 psi and heated to 150° C. while agitating. During the four hour reaction time, the pressure dropped from 3050 psi to 1100 psi. At the end of the reaction, the reactor was cooled to room temperature. A homogeneous solution (43.5 g) was recovered. The GC analysis showed the formation of N,N-diethylpropionamide (27g). The conversion of diethylamine was >95%. There was no other by-product observed. The reaction rate was calculated to be ca. 374 mole-product/g-atom Rh/hour. The off-gas analysis indicated the presence of CO 64.9%, $CO_2$ 7.5% and ethylene 15.5%.

EXAMPLE 2

The experimental procedures of Example 1 were repeated. The autoclave was charged with $Rh_2O_3 \cdot 5H_2O$ (0.025 g, 0.073 mmole), diethylamine (15.0 g, 205 mmoles), water (5.0 g) and ethylene (ca. 10.5g). The operating conditions were 150° C., 3000–1125 psi CO pressure and 4 hours. The GC analysis of recovered solution (ca. 36 g) showed the presence of N,N-diethylpropionamide as the only product. The off-gas analysis indicated CO 61%, $CO_2$ 19.3% and ethylene ca. 17.2%.

EXAMPLE 3

The experimental procedures of Example 1 were repeated. The reactor was charged with $Rh_2O_3 \cdot 5H_2O$ (0.025 g, 0.073 mmoles), diethylamine (5.0 g), methanol (10.0 g), water (5.0 g) and ethylene (13.0 g). The operating conditions were 150° C., 5050–2800 psi of CO and 4 hours. After the reaction, a homogeneous solution (ca. 37 g) was recovered. The GC analysis showed 24% N,N-diethylpropionamide in the reaction mixture (corresponding to ca. 8.8 g, 68 mmoles product). The analysis of GC-mass and Ft-IR indicated the presence of by-products, such as methyl propionate, 3-pentanone and 3,6-octanedione at the relative ratios of 17:15:5. These by-products were derived from the reaction of ethylene and CO in the presence of methanol.

EXAMPLE 4

The reactor was charged with $Rh_2O_3 \cdot 5H_2O$ (0.025 g, 0.073 mmole), diethylamine (15 g), methanol (10.0 g), water (5.0 g) and ethylene (11.0 g). The reaction conditions were 3300–1150 psi CO, 150° C. and 4 hours. The recovered solution (ca. 43.5, dark black) was analyzed by GC, indicating the presence of N,N-diethylpropionamide as the major product (ca. 81% yield).

EXAMPLE 5

An autoclave was charged with $Rh_2O_3 \cdot 5H_2O$ (0.025 g, 0.073 mmoles), methanol, (10.0 g), water (5.0 g), triethylamine (10.0 g) and ethylene (ca. 11 g). The reaction conditions were 900–1200 psi, CO pressure, 150° C. and 3 hours. The recovered solution (40.5 g) was analyzed by GC-FtIR and GC-mass. The following major products were identified: methyl propionate (ca. 34% selectivity), 3-pentanone (ca. 17% selectivity) and propionic acid (ca. 22% selectivity).

The reaction with methanol becomes predominant when a secondary amine is absent.

EXAMPLE 6

A working autoclave was charged with $Rh_2O_3 \cdot 5H_2O$ (0.025 g, 0.073 mmole), methanol (10.0 g), ammonium hydroxide (30%, 15 g) and ethylene (ca. 12 g). The reaction conditions were 3550–1300 psi CO pressure, 150° C. and 4 hours. The reaction mixtures were distilled to obtain ca. 10.5 g material, containing ca. 60% propionamide product as the major product. Another product was identified by H-nmr to be 2,4,5-triethylimidazole.

EXAMPLE 7

An autoclave was charged with $Rh_2O_3 \cdot 5H_2O$ (0.025 g), methanol (10 g), water (5.0 g), piperazine (10 g) and ethylene (10 g). The reaction conditions were 150° C., 2950–2800 psi of CO and 4 hours. The product solution was recovered in dark liquid (35.5 g) with 10.5 g weight gain. The portion of product solution (23.0 g) was subjected to vacuum distillation. In one fraction of distillation, N,N'-dipropionyl piperazine was obtained (ca. 5.5 g). In another fraction of distillation (ca. 1.0 g), a mixture of N-propionyl piperazine and N,N'-dipropionyl piperazine was obtained.

EXAMPLE 8

An autoclave was charged with $Rh_2O_3 \cdot 5H_2O$ (0.050 g), p-dioxane (15 g), 1-dodecene (8.4 g), diethylamine (3.5 g) and water (5 g). The reactor was purged of air with carbon monoxide, then pressured with carbon monoxide to 3000 psi at room temperature. The reaction mixture was heated to 160° C. for 4 hours. During the reaction process, the pressure changes from 4400 psi to 4125 psi, then to 4300 psi were recorded. (Note: The increase of pressure was due to water-gas-shift-reaction.) The recovered product solution (28.7 g) was analyzed by glc and H-nmr, showed only three products at ratios of 13:16:11 for I, II and III.

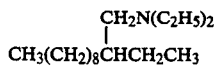  (I)

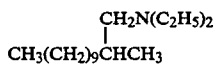  (II)

$CH_3(CH_2)_{11}CH_2N(C_2H_5)_2$  (III)

These tertiary amine products are derived from CO/$H_2$ reactions via water-gas-shift reaction. These side reactions dominated over the amide formation under the specific reaction conditions of higher pressure and less reactive olefin.

What is claimed is:

1. In a process for producing N,N-diethylpropionamide from ethylene, diethylamine and synthesis gas, the improvement comprising effecting the reaction in the presence of a catalyst comprising hydrated rhodium (III) oxide in water at a pressure of 1000 psi to 4000 psi and temperature of 80° C. to 200° C.

2. In a process for producing N-alkyl amides by reacting olefins, nitrogen-containing compounds and synthesis gas, the improvement comprising reacting an olefin from the group consisting of ethylene propylene and 1-butene with a nitrogen-containing compound from the group consisting of diethylamine and piperazine in the presence of a catalyst comprising hydrated rhodium (III) oxide in water at a pressure of 1000 psi to 4000 psi and a temperature of 80° C. to 200° C.

3. A process for producing propionamide by reacting ethylene, ammonium hydroxide and synthesis gas in the presence of a catalyst comprising hydrated rhodium-(III) oxide in water at a pressure of 1000 psi to 4000 psi and at a temperature of 80° C. to 200° C.

4. A process for producing N,N'-dipropionyl piperazine by reacting ethylene, piperazine and carbon monoxide in the presence of a catalyst comprising hydrated rhodium(III) oxide in water at a pressure of 1000 psi to 4000 psi and a temperature of 80° C. to 200° C.

* * * * *